United States Patent [19]

Tsao et al.

[11] Patent Number: 4,908,147
[45] Date of Patent: Mar. 13, 1990

[54] AQUEOUS SELF PRESERVING SOFT CONTACT LENS SOLUTION AND METHOD

[75] Inventors: Fupao Tsao, Lawrenceville; Allen Penley, Atlanta, both of Ga.

[73] Assignee: Ciba-Geigy Corporation, Ardsley, N.Y.

[21] Appl. No.: 324,957

[22] Filed: Mar. 16, 1989

Related U.S. Application Data

[63] Continuation of Ser. No. 211,068, Jun. 20, 1988, abandoned, which is a continuation of Ser. No. 67,421, Jun. 24, 1987, abandoned, which is a continuation of Ser. No. 831,221, Feb. 19, 1986, abandoned.

[51] Int. Cl.$^4$ .............................................. C11D 1/92
[52] U.S. Cl. ..................................... 252/106; 252/545; 252/546; 252/DIG. 14; 514/554; 514/939
[58] Field of Search ............... 252/106, 173, 547, 545, 252/546, DIG. 14; 514/939, 554

[56] References Cited

U.S. PATENT DOCUMENTS

| | | | |
|---|---|---|---|
| 3,001,996 | 9/1961 | Mannheimer | 252/106 |
| 3,380,923 | 4/1968 | Beach | 252/106 |
| 3,928,251 | 12/1975 | Bolich et al. | 252/545 |
| 3,991,208 | 11/1976 | Dudzinski et al. | 514/554 |
| 4,013,576 | 3/1977 | Loshaek | 252/106 |
| 4,046,706 | 9/1977 | Krezanoski | 252/106 |
| 4,104,187 | 8/1978 | Sibley et al. | 252/106 |
| 4,137,191 | 1/1979 | Lohr | 252/153 |
| 4,354,952 | 10/1982 | Riedhammer et al. | 252/106 |
| 4,414,127 | 11/1983 | Fu | 252/95 |
| 4,510,065 | 4/1985 | Sherman | 252/106 |
| 4,584,121 | 4/1986 | Blaschke et al. | 252/106 |
| 4,655,957 | 4/1987 | Chromecek et al. | 252/174.23 |
| 4,738,790 | 4/1988 | Miyajima et al. | 252/105 |
| 4,758,595 | 7/1988 | Ogunbiyi et al. | 514/635 |

FOREIGN PATENT DOCUMENTS

| | | |
|---|---|---|
| 3091184 | 1/1985 | Australia . |
| 4759985 | 4/1986 | Australia . |
| 5084485 | 6/1986 | Australia . |
| 5084585 | 6/1986 | Australia . |

OTHER PUBLICATIONS

Y. Abe, S. Osanai, and S. Matsummura, J. Am. Oil Chem. Soc., 49:347 (1972), pp. 357-360.
Bluestein et al., "Amphoteric Surfactants", vol. 12, 1982, Marcel Dekker, Inc., N.Y. pp. 216-218.

*Primary Examiner*—Prince E. Willis
*Attorney, Agent, or Firm*—Irving M. Fishman

[57] ABSTRACT

A method for cleaning or preserving a soft contact lens comprising intimately contacting said soft contact lens with an aqueous solution containing an effective surfactant and solution preservative amount of an amphoteric surfactant of the formula:

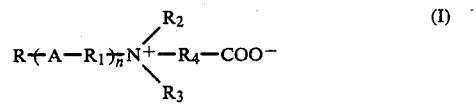

wherein
R is alkyl, alkenyl or alkanedienyl of six to eighteen carbon atoms which may be substituted;
A is —O—, —S—,

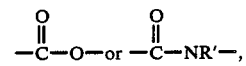

where R' is hydrogen or lower alkyl;
$R_1$ is alkylene of 2 to 6 carbon atoms, which is unsubstituted or substituted by hydroxy;
n is 0 or 1;
$R_2$ and $R_3$ are independently hydrogen or lower alkyl which is unsubstituted or substituted by carboxy or one or two hydroxyls, one of which may be esterified with phosphoric or sulfuric acid; and
$R_4$ is alkylene of up to 3 carbon atoms, which is unsubstituted or substituted by hydroxy; and the ophthalmologically acceptable salts thereof; and compositions for use in such methods.

9 Claims, No Drawings

AQUEOUS SELF PRESERVING SOFT CONTACT LENS SOLUTION AND METHOD

This application is a continuation of application Ser. No. 211,068, filed 06/20/88, which is a continuation of Ser. No. 067,421 filed 6/24/84, which is a continuation of Ser. No. 831,221 all now abandoned.

BACKGROUND OF THE INVENTION

The present invention relates to a method for cleaning or preserving a soft hydrophilic contact lens using an amphoteric surfactant which also serves as a solution preservative.

A number of contact lens cleaner solutions are known in the art. Typically such solutions employ either sorbic acid, thimerosal, chlorhexidine, a polyquaternary germicide, a synthetic antibiotic or a conventional quaternary germicide, such as benzalkonium chloride as a preservative agent. However, these conventional preservatives have drawbacks that tend to restrict their use. For example, sorbic acid characteristically contains formaldehyde residues; thimerosal in some patients acts as an allergy sensitizer, chlorhexidine is relatively toxic; and benzalkonium chloride, over a period of time, will tend to accumulate in soft hydrophilic contact lens materials and tend to release to the cornea to cause eye irritation.

While U.S. Pat. No. 4,046,706 discloses the use of certain amphoteric imidazole surfactants in lens-cleaning solutions, such solutions characteristically also require the presence of a germicidal preservative agent of the type discussed above.

Surprisingly and unexpectedly, it has now been found that, while the instant amphoteric surfactant solutions contain a quaternary nitrogen, they do not appreciably build up or accumulate in conventional hydrophilic soft contact lenses. This is in clear contrast to conventional quaternary germicides, such as benzalkonium chlorides (i.e., alkyl substituted dimethylbenzyl ammonium chloride wherein alkyl is a mixture of $C_8$ to $C_{18}$ alkyl moieties), cetylpyridinium chloride and dodecyl triethanolamine hydrochloride, which tend to accumulate in hydrophilic soft contact lens materials. Moreover, the instant amphoteric surfactants do not tend to accumulate in the eye and are characteristically less irritating than such conventional quaternary germicides.

It is therefore an object of the present invention of overcoming the various drawbacks associated with the use of prior art soft contact lens-cleaning solutions.

It is a further object of the present invention to provide a method for preserving and cleaning soft hydrophilic contact lenses using an effective surfactant and solution preservative amount of the instant amphoteric surfactants.

It is yet a further object of the present invention to provide compositions useful in such methods and their preparation.

These and other objects of the present invention are apparent from the following detailed disclosures.

DETAILED DESCRIPTION OF THE INVENTION

One embodiment of the instant invention relates to a method for cleaning a soft contact lens comprising intimately contacting said soft contact lens with an aqueous solution containing an effective surfactant and solution preservative amount of a water-soluble amphoteric surfactant of the formula.

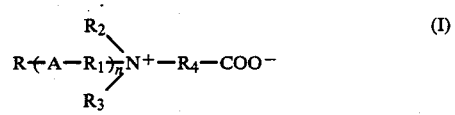

wherein
R is alkyl, alkenyl or alkanedienyl of 6 to 18 carbon atoms which are unsubstituted or is substituted by halo, hydroxy or amino;
A is —O—, —S—,

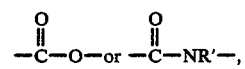

where R' is hydrogen or lower alkyl;
$R_1$ is alkylene of 2 to 6 carbon atoms which is unsubstituted or substituted by hydroxy;
n is 0 or 1;
$R_2$ and $R_3$ are independently hydrogen or lower alkyl, which is unsubstituted or substituted by carboxy or by one or two hydroxyls, one of which may be esterified with phosphoric or sulfuric acid; and
$R_4$ is alkylene of up to 3 carbon atoms which is unsubstituted or substituted by hydroxy; and the ophthalmologically acceptable salts thereof.

Preferably, R is alkyl or alkenyl of 8 to 18 carbon atoms, or a mixture thereof.

Where n is 1, A is preferably —CONH— and $R_1$ is alkylene of 2 to 3 carbon atoms. In an alternate preferred embodiment, n is 0.

$R_2$ and $R_3$ are preferably independently lower alkyl which is unsubstituted or mono- or di-substituted with hydroxy, one hydroxy of which may be esterified with phosphoric acid to form the corresponding mono-, di- or tri-organophosphate ester.

$R_4$ is preferably unsubstituted straight chain or branched chain alkylene of up to 3 carbon atoms and, most preferably, is —$CH_2$—, —$CH_2CH_2$—, —$CH(CH_3)$—, —$CH_2CH_2CH_2$— or —$CH(CH_3)$—$CH_2$—. As an alternate preferred embodiment, $R_4$ is —$CH_2CH(OH)CH_2$—.

Suitably ophthalmologically acceptable salts are salts formed by the compounds of formula I with sodium chloride, potassium chloride, sodium phosphate, sodium borate, sodium bicarbonate, carbonic acid, boric acid, diethanolamine and analogous inorganic and organic acids, bases and salts conventionally employed in lens-care solutions. As the artisan can appreciate, where salts such as sodium chloride are employed, the zwitterionic inner salt form may be in equilibrium with the corresponding double salt form.

Also, aqueous self-preserving soft contact lens-cleaning solutions, according to this embodiment of the invention, may contain, in addition to the compound of formula I, other conventional additives and adjuvants. For example, suitable self-preserving cleaning solutions, according to the instant invention, include those preferably containing, based on the total solution weight:
(a) between about 0.005 to about 2.0% by weight compound of formula I;
(b) between 0 to about 5% by weight of a substantially nonionic surfactant;
(c) between 0 to about 5% by weight of a thickener;

(d) between 0 to about 1% by weight of a chelating agent;
(e) between 0 to about 2% by weight of a buffer;
(f) between 0 to about 2% by weight of a water-soluble, salt compatible with ocular tissue, and
(g) the remainder water.

Preferably, the compositions for use in the instant invention contain between about 0.01 to about 0.5%, most preferably between about 0.02 to about 0.2% by weight compound of formula I.

When present, each of the optional components (b) through (f) are advantageously present in a minimum amount of about 0.01% by weight based on total solution weight.

Suitable substantially nonionic surfactants for use as component (b) advantageiously include those nonionic surfactats which are known to be generally compatible with ocular tissue, and include physiologically acceptable poly(oxyethylene)-poly(oxypropylene) block copolymers, such as those sold under the trademark "PLURONIC" by Wyandotte Chemical Corporation. Such copolymers are represented empirically by the formula:

$$HO(CH_2CH_2O)_a(CH(CH_3)CH_2O)_b(CH_2CH_2O)_cH$$

where a and c are statistically equal, the average molecular weight ranges between about 2,000 and about 16,000, and the polyoxyethylene units constitute between about 10% and 80% by weight of the molecule.

Also suitable are polyethoxylated alkylphenols, for example, wherein the alkyl moiety thereof contains between about 6 and 12 carbon atoms, and there are between about 3 and about 50 polyoxyethylene units per molecule, as well as the corresponding alkylated methylene bis-phenols which are polyethoxylated, such as that sold under the name "TYLOXAPOL," by Ruger Chemical Co.

Also suitable are polyethoxylated fatty alcohols, acids, amines, e.g. wherein the alkyl moiety thereof contains between 6 and 18 carbon atoms and the molecule contains an average of between about 3 and about 50 polyoxyethylene units. Preferably, the instant compositions contain between 0 and about 0.5% by weight of component (b).

Suitable thickeners (c) include those conventionally employed in ophthalmic formulations and include, for example, hydroxyethylcellulose, hydroxypropylcellulose, polyvinylalcohol, polyvinylpyrollidone, polyethyleneglycol and the like. Preferably, a thickener is present in an amount between 0% and about 2% by weight, more preferably between 0% and about 1.5% by weight.

Suitable chelating agents (d) include conventional chelating agents such as ethylenediamine tetracetic acid and the alkali metal, e.g. di- and tri-sodium salts thereof, and trihydroxymethyl aminomethane. Preferably, the chelating agent is present in an amount between 0 and about 0.7% by weight.

Suitable buffers (e) include alkali metal phosphates, citrates, borates, tartrates, acetates, carbonates, bicarbonates and the corresponding phosphoric acid, citric acid, boric acid, tartaric acid, and mixtures thereof. Preferably, buffers are present in an amount between 0 and about 1% by weight.

Suitable water soluble salts compatible with ocular tissue (f) include especially those salts conventionally employed in providing solutions having a salt content equivalent to up to about 0.9% sodium chloride. Preferred salts are alkali metal halides, sulfates, nitrates, and phosphate salts, especially sodium chloride, potassium chloride, and mixtures thereof.

An alternate embodiment of the instant invention relates to a method of preserving a soft contact lens by storing said lens in an aqueous solution containing a solution preservative amount of the compound of formula I and a sufficient amount of a water-soluble salt, compatible with ocular tissue, to provide a solution salt content equivalent in tonicity to about 0.5% to about 2% by weight sodium chloride.

In this alternate embodiment, it is preferred to have a sufficient amount of salt content to provide a solution salt content equivalent in tonicity to between about 0.7 and about 1.8%, and most preferably between about 0.7 and about 1.0%, by weight sodium chloride.

Suitable salts which may be employed in adjusting the tonicity include alkali metal halides, sulfates, nitrates, phosphates and the like, especially the sodium and potassium salts thereof and most preferably sodium chloride, potassium chloride and mixtures thereof.

The lens preserving and storing solutions, in accordance with this embodiment, can generally contain the same additives and adjuvants in the same ranges set forth above in respect to the self-preserving contact lens-cleaning solutions, except that the lens-preserving and storing solutions advantageously contain a sufficient amount of component (f) salt to provide a solution salt content equivalent in tonicity to between about 0.7 and about 1.8% by weight sodium chloride.

A convenient method of cleaning the contact lenses according to the instant invention, is to place the lens in the palm of the hand, place a few drops of solution on each lens surface, and rub the lens surfaces with the forefinger or between the thumb and forefinger, and rinse with additional solution.

The instant solutions are useful for cleaning proteinaceous, lipid and other non-proteinaceous deposits which normally accumulate on conventional hydrophilic soft contact lenses. These deposits, derived from mucus, oils, cosmetics, protein from tear fluid, and the like, unless removed, will tend to accumulate on the lenses, reducing the life of such lenses and their optical clarity. The instant compositions are highly useful in removing and solubilizing such deposits while, at the same time, are physiologically tolerable and self-preserving.

Further, the preferred instant lens-storing and preserving solutions are additionally advantageous in that the tonicity of such compositions, coupled with the nonirritating nature of the compounds of formula I to the eye, and their reduced tendency to accumulate in soft hydrophilic contact lens materials, make such compositions highly advantageous as preservative lens media, from which the lens can be placed directly into the eye without rinsing with a conventional saline solution.

The compositions of the instant invention are prepared from materials known, per se. Thus, the compounds of formula I belong to a known class of ampho- teric surfactants.

Highly preferred compounds of formula I include:
N-laurylamidopropyl, N,N-dimethyl glycine;
N-cocamidopropyl, N,N-dimethyl glycine;
N-laurylamidopropyl, N-carboxymethyl, N-hydroxyethyl glycine;
N-oleylamidopropyl, N-carboxymethyl, N-hydroxyethyl glycine;

N-coco, N,N-dimethyl glycine;
N-oleyl, N,N-dimethyl glycine
N-3-dodecyloxy-2-hydroxypropyl, N,N-dimethyl glycine;
N-cocoamidopropyl N-hydroxyethyl 3-aminopropionic acid;
N-dodecyl, N,N-dimethyl glycine; and
tri(3-[N-cocoamidoethyl, N-hydroxyethyl, N-carboxymethyl]-amino-2-hydroxy-propanol)phosphate.

The following examples are for illustrative purposes and are not intended to limit the scope of the invention. In each instance all percentages and parts are by weight unless otherwise specified.

EXAMPLE 1

0.5 Ml of an aqueous solution containing 30 percent by weight N-cocoamidopropyl, N,N-dimethyl glycine (Monateric ® CAB by Mona Industries, Inc.) was combined with 2.613 g sodium chloride, 1.25 g sodium tetraborate, 1.75 g boric acid, 1.0 ml tyloxapol, 3.5 g hydroxyethyl cellulose and 2.5 g disodium edetate, and water added to a total solution of 500 ml with stirring. The resulting solution was filter sterilized using ultrafiltration to obtain a solution having a pH of 7.2 and an osmolarity of 304.

EXAMPLE 2

0.5 Ml of an aqueous solution containing 30 percent by weight N-laurylamidopropyl,N,N-dimethyl glycine (Monateric ® LMAB) was combined with 2.685 g sodium chloride, 1.25 g tyloxapol, 3.5 g hydroxylethyl cellulose, and 2.5 grams of disodium edetate and water added to a total solution volume of 500 ml with stirring. The resulting solution was filter sterilized using ultrafiltration to obtain a solution having a pH of 7.2 and an osmolarity of 298.

EXAMPLE 3

0.5 Ml of an aqueious solution containing 30 percent by weight N-cocoamidopropyl,N,N-dimethyl glycine was combined with 3.45 g sodium chloride, 0.7 g sodium tetraborate, 2.7 g boric acid and 1.0 g disodium edetate, and water added to a total solution volume of 500 ml with stirring. The resulting solution was filter sterilized using ultrafiltration to obtain a solution having a pH of 7.2 and an osmolarity of 306.

EXAMPLE 4

0.5 Ml of an aqueous solution containing 30 percent by weight N-laurylamidopropyl, N,N-dimethyl glycine was combined with 3,18 g sodium chloride, 0.7 g sodium tetraborate, 2.7 g boric acid and 1.0 g disodium edetate, and water added to a total solution volume of 500 ml with stirring. The resulting solution was filter sterilized using ultrafiltration to obtain a solution having a pH of 7.21 and an osmolarity of 310.

EXAMPLE 5

0.25 G of an aqueous solution containing 35 weight percent of N-oleyl N,N-dimethyl glycine (Mirataine ® ODMB by Miranol Chemical Co.) was combined with 2.67 g sodium chloride, 1.25 g sodium borate, 1.75 g boric acid, 1.0 g tyloxapol, and 3.5 g hydroxyethyl cellulose, and sufficient water added to obtain a total solution volume of 500 ml. The solution was adjusted to a pH of 7.21 using 0.5N HCL and was filter sterilized using ultrafiltration. The resulting solution had an osmolarity of 302.

EXAMPLE 6

0.3 G of an aqueous solution containing 30 weight percent of tri-(3-[N-cocoamidoethyl, N-hydroxyethyl, N-carboxymethyl]amino-2-hydroxypropanol)phosphate (Monaquat P-TL by Mona Industries, Inc.) is combined with 0.24 g tris-(hydroxymetyl)aminomethane, 1.0 g boric acid and 0.36 g sodium chloride and diluted with sufficient water to obtain a total solution volume of 100 ml.

EXAMPLE 7

1.5 G of an aqueous solution containing 30 percent by weight N-laurylamidopropyl, N,N-dimethyl glycine, 2.685 g sodium chloride, 1.25 g sodium tetraborate, 1.75 g boric acid, 1.0 g tyloxapol, 3.5 g hydroxyethylcellulose, and 2.5 g disodium edetate were combined and sufficient water added with stirring to obtain a total solution volume of 500 ml. The pH of the solution was 7.03, which was adjusted with 0.5N HCl to a pH of 7.23.

EXAMPLE 8

The procedure of Example 7 was repeated and identical amounts of ingredients were used except that 2.5 g of an aqueous solution containing 30 percent by weight N-laurylamidopropyl-N,N-dimethyl glycine was employed. Upon dilution to S500 ml wit water, the pH was 7.4 which was adjusted with 0.5N HCl to a pH of 7.20.

EXAMPLE 9

1.5 G of an aqueous solution containing 30 percent by weight N-laurylamidopropyl-N,N-dimethyl glycine, 1 g disodium edetate, 2.7 g boric acid, 0.70 g sodium borate and 3.15 g sodium chloride were combined and diluted with sufficient water, with stirring, to make a total solution volume of 500 ml. The solution had a pH of 7.22 and an osmolarity of 319.

EXAMPLE 10

The compositions of Examples 7, 8 and 9 were evaluated in accordance with the modified Draize rabbit eye test (Food, Drug, and Cosmetic Law Reports 233) in order to access potential irritation. The three solutions were each determined to be "non-irritating" in this test.

What is claimed is:

1. An aqueous self-preserving soft contact lens cleaning or preserving solution comprising, as its only preservative agent, an effective surfactant and solution preserving amount of an amphoteric surfactant of the formula

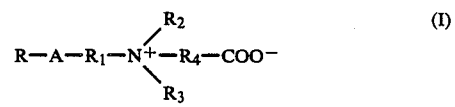

wherein
R is alkyl, alkenyl or alkanedienyl of six to eighteen carbon atoms which are unsubstituted or substituted by halo, amino or hydroxy;
A is —O—, —S—,

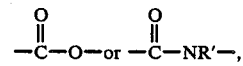

where R' is hydrogen or lower alkyl;

$R_1$ is alkylene of 2 to 6 carbon atoms, which is unsubstituted or substituted by hydroxy;

$R_2$ and $R_3$ are independently hydrogen or lower alkyl which is unsubstituted or substituted by one or two hydroxyls, one of which may be esterified with phosphoric or sulfuric acid; and $R_4$ is alkylene of up to 3 carbon atoms, which is unsubstituted or substituted by hydroxy; and the ophthalmologically acceptable salts thereof; and water, said solution having a pH such that upon removing a contact lens from said solution, said contact lens is capable of being placed directly on the eye without rinsing and without causing significant irritation to the eye on which said lens is placed.

2. A solution according to claim 1, wherein R is unsubstituted alkyl or alkenyl of 8 to 12 carbon atoms.

3. A solution according to claim 2, wherein A is —CONH— and $R_1$ is akylene of 2 to 3 carbon atoms.

4. A solution according to claim 3, wherein $R_4$ is unsubstituted alkylene of up to 3 carbon atoms.

5. A solution according to claim 4, wherein $R_2$ and $R_3$ are unsubstituted lower alkyl.

6. A solution according to claim 5, wherein $R_2$ and $R_4$ are methyl.

7. The solution of claim 1 further comprising an ophthalmologically acceptable water soluble salt which is compatable with ocular tissue to provide a solution salt content equivalent in tonicity to about 0.5 to 2.0% by weight sodium chloride.

8. The solution of claim 1 wherein said pH is about 7.2.

9. A method of cleaning or preserving a soft contact lens comprising intimately contacting said soft contact lens with a solution according to claim 1.

* * * * *